US009606104B2

(12) United States Patent
Xu et al.

(10) Patent No.: US 9,606,104 B2
(45) Date of Patent: *Mar. 28, 2017

(54) AUTOMATED PLATELET FUNCTION ANALYZER AND ITS ANALYTICAL METHODS

(71) Applicant: Sinnowa Medical Science & Technology Co., Ltd., Nanjing, Jiangsu (CN)

(72) Inventors: Xin Xu, Nanjing (CN); Ziquan Dong, Nanjing (CN); Ning Cao, Nanjing (CN); Xiang Li, Nanjing (CN); Fan Yu, Nanjing (CN); Weijie Yang, Nanjing (CN)

(73) Assignee: Sinnowa Medical Science & Technology Co., Ltd., Nanjing, Jiangsu (CN)

( * ) Notice: Subject to any disclaimer, the term of this patent is extended or adjusted under 35 U.S.C. 154(b) by 0 days.

This patent is subject to a terminal disclaimer.

(21) Appl. No.: 15/041,453

(22) Filed: Feb. 11, 2016

(65) Prior Publication Data

US 2016/0161467 A1 Jun. 9, 2016

Related U.S. Application Data

(60) Continuation-in-part of application No. 14/154,666, filed on Jan. 14, 2014, now Pat. No. 9,291,632, which
(Continued)

(51) Int. Cl.
*G01N 33/49* (2006.01)
*G01N 35/10* (2006.01)
(Continued)

(52) U.S. Cl.
CPC .......... *G01N 33/49* (2013.01); *A61B 5/1405* (2013.01); *A61B 5/1427* (2013.01); *A61B 5/153* (2013.01);
(Continued)

(58) Field of Classification Search
CPC ...... G01N 35/1004; G01N 2035/00544; A61B 5/150229; A61B 5/1405; A61B 5/15003;
(Continued)

(56) References Cited

U.S. PATENT DOCUMENTS 4,729,876 A * 3/1988 Hennessy .......... G01N 35/1097
422/539
5,358,641 A * 10/1994 Sanford ................ G01N 30/32
210/198.2
(Continued)

FOREIGN PATENT DOCUMENTS

| CN | 2695975 | 4/2005 |
| CN | 202126438 | 1/2012 |
| WO | 2006/116699 | 11/2006 |

*Primary Examiner* — Rebecca M Fritchman
(74) *Attorney, Agent, or Firm* — Rankin, Hill & Clark LLP (57) ABSTRACT

An automated platelet function analyzer includes a sampling vessel, a preparation vessel, an analysis vessel, a sampling needle, an analysis solution syringe, a detergent syringe, and blood mixing devices. The sampling vessel is placed in a sample holder, which vacillates left and right. A method for platelet analysis is also disclosed.

9 Claims, 5 Drawing Sheets

Related U.S. Application Data is a division of application No. 13/641,484, filed as application No. PCT/CN2011/077120 on Jul. 13, 2011, now abandoned.

(51) Int. Cl.
*A61B 5/15* (2006.01)
*A61B 5/155* (2006.01)
*A61B 5/153* (2006.01)
*A61B 5/157* (2006.01)
*G01N 33/86* (2006.01)
*G01N 15/10* (2006.01)
*G01N 35/00* (2006.01)
*G01N 15/00* (2006.01)

(52) U.S. Cl.
CPC .......... *A61B 5/15003* (2013.01); *A61B 5/155* (2013.01); *A61B 5/157* (2013.01); *A61B 5/150221* (2013.01); *A61B 5/150229* (2013.01); *A61B 5/150755* (2013.01); *A61B 5/150992* (2013.01); *G01N 15/10* (2013.01); *G01N 33/86* (2013.01); *G01N 35/1065* (2013.01); *G01N 35/1004* (2013.01); *G01N 2015/0084* (2013.01); *G01N 2015/0092* (2013.01); *G01N 2015/1062* (2013.01); *G01N 2035/00534* (2013.01); *G01N 2035/00544* (2013.01)

(58) Field of Classification Search
CPC ........ A61B 5/150221; A61B 5/150755; A61B 5/153; A61B 5/155
USPC ......................................... 422/73; 435/287.1
See application file for complete search history.

(56) References Cited

U.S. PATENT DOCUMENTS

| | | |
|---|---|---|
| 5,716,796 A | 2/1998 | Bull et al. |
| 6,043,871 A | 3/2000 | Solen et al. |
| 6,123,119 A | 9/2000 | Okumura |
| 2006/0166373 A1 | 7/2006 | Enoki et al. |
| 2006/0246528 A1 | 11/2006 | Swaim et al. |
| 2009/0068726 A1 | 3/2009 | Magnin et al. |
| 2011/0178359 A1* | 7/2011 | Hirschman ............ A61B 6/037 600/4 |

* cited by examiner

AUTOMATED PLATELET FUNCTION ANALYZER AND ITS ANALYTICAL METHODS

FIELD OF THE INVENTION

The present invention relates to medical equipment and its analytical methods, more particularly to an automated platelet function analyzer and its analytical methods, which can be used to rapidly and consecutively detect the changes of blood platelet aggregation.

BACKGROUND OF INVENTION

Platelet, a type of particle blood constituent, is an important factor for the blood hemostasis and thrombosis. Conveniently and efficiently determining the numbers, volume, aggregation rate and other parameters of platelet, plays a significant role in the diagnosis, prophylaxis and treatment guidance of thrombosis and related diseases. With the development of technology and in-depth study on platelet, some of the single platelet category or functional testing instrument has been developed in various countries. Such as: existing platelet aggregation analyzer (just a single function to measure the platelet aggregation parameters, the existing analytical instruments mainly based on the principle of turbidimetric method or direct method by measuring the electrode resistance), hematology analyzers or blood cell analyzer (such equipment can only determine the platelet numbers, volume and so on, and not have the ability to measure the same blood platelet repeatedly, consecutively and automatically. That is to say they are unable to determine the platelet aggregation automatically). Therefore, so far an analytical instrument to determine the platelet aggregation rate based on the principle of automatically and consecutively measuring the blood platelets changes in blood sample treated by platelet agonist do not exist. There is no instrument to measure the platelet numbers, volume automatically and further determine the platelet aggregation rate and other multiple parameters simultaneously.

Traditional detection principle used by the platelet aggregation instrument is optical turbidimetry method or electric resistance method. Platelet aggregation detector based on optical turbidimetry method is more common. However, this detector needs a larger amount of blood (2 ml whole blood usually). Before examination it still is pre-requisite to separate plasma, which is a complicated and time-consuming operation. Platelet aggregation analyzer based on resistance method achieves the platelet aggregation rate by measurement of platelet aggregation changes on the electrode, which also needs more than 2 ml whole blood. Furthermore, both methods described above are rarely for clinical use due to a poor reproducibility.

SUMMARY OF THE INVENTION

The object of this present invention is to solve the technical problems of the prior art by providing an automated platelet function analyzer and its analytical methods.

To solve the technical problems mentioned above, the present invention discloses an automated platelet function analyzer including a sampling vessel, a preparation vessel, an analysis vessel, a sampling needle, a sample syringe, an analysis solution syringe, a detergent syringe, blood mixing devices, et al.

The sampling vessel is used to store blood samples and also as a platelet aggregation reaction container. Generally the volume of the sampling vessel is 1-5 ml and the sample volume added by the sampling needle, or manually prepared.

The preparation vessel is used for the first blood sample dilution. Generally the volume of the preparation vessel is 1-20 ml and the sample volume added by the sampling needle or the blood sample syringe is 8-200 µl each time. The volume of the first dilution is 50 to 300 times of the sample volume dispensed.

The analysis vessel is used for the second blood dilution and the platelet number detection. Generally the analysis vessel volume is 1-20 ml. The volume of the second dilution is 50 to 300 times of the sample volume dispensed.

After the second dilution, the final concentration of platelets is $1/90000$-$1/10000$ of the original blood samples.

The sampling vessel is placed in the position of sample holder, which keeps vacillating left and right, and it's vacillating to each side will be within the angle 90°, so the blood in the sampling vessel will be kept in good mixed situation and the blood in the vessel will not overflow out of the sampling vessel The sampling vessel is a single use cuvette and is kept opened during the testing process, so the vessel will be easy for taking sample out and adding reagent into during the testing process. The sample holder will be stopped for moment during sample needle taking sample or adding reagent.

The sample holder has heating and temperature control function, so it makes the sampling vessel in controlled temperature state.

The blood mixing devices are used for mixing the blood samples in the preparation vessel and the analysis vessel.

The sampling syringe is connected to the sampling needle, which work together with the related valve\pipe, can take sample from one vessel to another one, and also can take platelet agonists from the agonist container and inject platelet agonists into the sampling vessel.

The analysis solution syringe is connected to the analysis solution container to inject the analysis solution to the preparation vessel, the analysis vessel and the sampling needle.

The movement of the sampling needle, the sample syringe, the detergent syringe and the analysis solution syringe are driven by motors.

After the sampling needle is connected to blood sample syringe, which takes the quantitative sample from the sampling vessel and transferring it to preparation vessel, absorbing the diluted blood samples from preparation vessel and transferring it to the analysis vessel.

Or the sampling needle firstly takes the blood sample from outside of the analyzer, and then adds the blood sample in sequence to the sampling vessel, absorbs blood samples from sampling vessel and transfers the blood sample to preparation vessel, absorbs the diluted blood samples from preparation vessel and transfers the diluted blood samples to the analysis vessel.

After the analysis solution syringe is connected to the said sampling needle, the sampling needle will be cleaned.

The mixing device according to the present invention is air pump, which is separately connected to the preparation vessel and the analysis vessel through pipes and valves.

The internal diameter of pipe, which connected to preparation vessel and analysis vessel, is 0.2 mm-2 mm, and its inlet air flow rate is 1-2000 ml/min.

The preferred air pump according to the present invention are a rotary pump or a mixing syringe.

The present invention as described includes a cleaner which is used to clean the outer surface of sampling needle. The cleaner automatically cleans the residual blood of the sampling needle surface every time after analysis to prevent the residual blood of the sampling needle surface from affecting the data analysis.

Preferably the present invention includes a waste liquid pump, which is connected to the preparation vessel, the analysis vessel and the cleaner. The waste liquid pump cleans each vessel and empties the residual object when the corresponding analysis is completed The present invention also discloses a platelet analysis method which includes the following steps:

Step 1: connecting the sampling needle and blood sample syringe, absorbing the blood sample and transferring it to the sampling vessel and mixing;

Step 2: by sampling needle and blood sample syringe quantitatively absorbing the blood sample from the sampling vessel, and then transferring it to preparation vessel;

Step 3: transferring the analysis solution to the preparation vessel, quantitatively making the first dilution by the analysis solution syringe and mixing;

Step 4: connecting the sampling needle to blood sample syringe, quantitatively, absorbing the blood sample from the preparation vessel and transferring it to the analysis vessel;

Step 5: transferring analysis solution to the analysis vessel by the analysis solution syringe, quantitatively making a second dilution and mixing;

Step 6: counting the original platelet numbers of the blood sample in the analysis vessel;

Step 7: dispensing the platelet agonist into the sampling vessel and mixing; the volume ratio between the blood sample and the platelet agonist is 1:1-20:1; generally the platelet agonist is the aqueous solution of adenosine diphosphate or arachidonic acid, or epinephrine.

Step 8: repeating step 2 to step 5 with a certain time interval and counting the platelet numbers of the blood sample at each time point after dispensing the platelet agonist. The common interval is 30-300 s.

Step 9: comparing the numbers of platelet after dispensing platelet agonist at each time point with that of original platelet to achieve the platelet aggregation rate.

In consideration of the analysis accuracy and analysis equipment volume, the present invention adopts twice dilution method using the preparation vessel and the analysis vessel to complete the dilution. Compared to the traditional method of once dilution, this dilution has better detection accuracy.

In the present invention, preferably the blowing-air method is adopted to mix the blood samples in the preparation vessel and the analysis vessel. Traditional platelet analysis equipment can only analyze the numbers of platelets statically, which is unable to analyze the platelet aggregation ability at a certain time consecutively. Because there will be inhomogeneous platelet after a certain period of time, through a large number of comparative study the applicant of the present invention found the analysis results by blowing-air method is the most accurate. Certainly, mechanically stirring method, using sampling needle or other straw suction method can also mix the blood samples to be analyzed.

In the present invention, the analysis solution should not affect the platelet aggregation in blood samples, react with any component of the blood, and contain any particles of impurities. Generally, deionized physiological saline or analysis solution available on the market for blood cell analyzer can be accepted. The preferred analysis solution is of osmotic pressure similar to blood osmotic pressure.

In the present invention, the platelets information obtained after the first detection is the original state information. Thereafter the differences of detection due to platelet aggregation in blood samples will reflect individual platelet number and volume changes in the blood samples after the platelet agonist is dispensed, and then the original platelet numbers, volume and platelet aggregation change after dispensing the platelet agonist will be obtained.

Beneficial effects: a prominent advantage of the present invention lies in using of whole blood directly and finishing the detection of the platelet aggregation rate without the separation of plasma. Furthermore required blood is less (less than 500 ul). Able to obtain test results of each time point in a certain time by the direct detection of platelet number changes before and after dispensing platelet agonist and consecutive detection, the result of detection at each time point of a period can be achieved. The instrument detection process is completely automated, so the detection is convenient, fast, and rarely susceptible to human factors.

BRIEF DESCRIPTION OF THE DRAWINGS

The present invention will now be further described by referring to the accompanying drawings that illustrate the preferred embodiments of the invention, from which its advantages described above and/or other advantages will be evident.

DETAILED DESCRIPTION OF THE EMBODIMENTS

Figure 1:
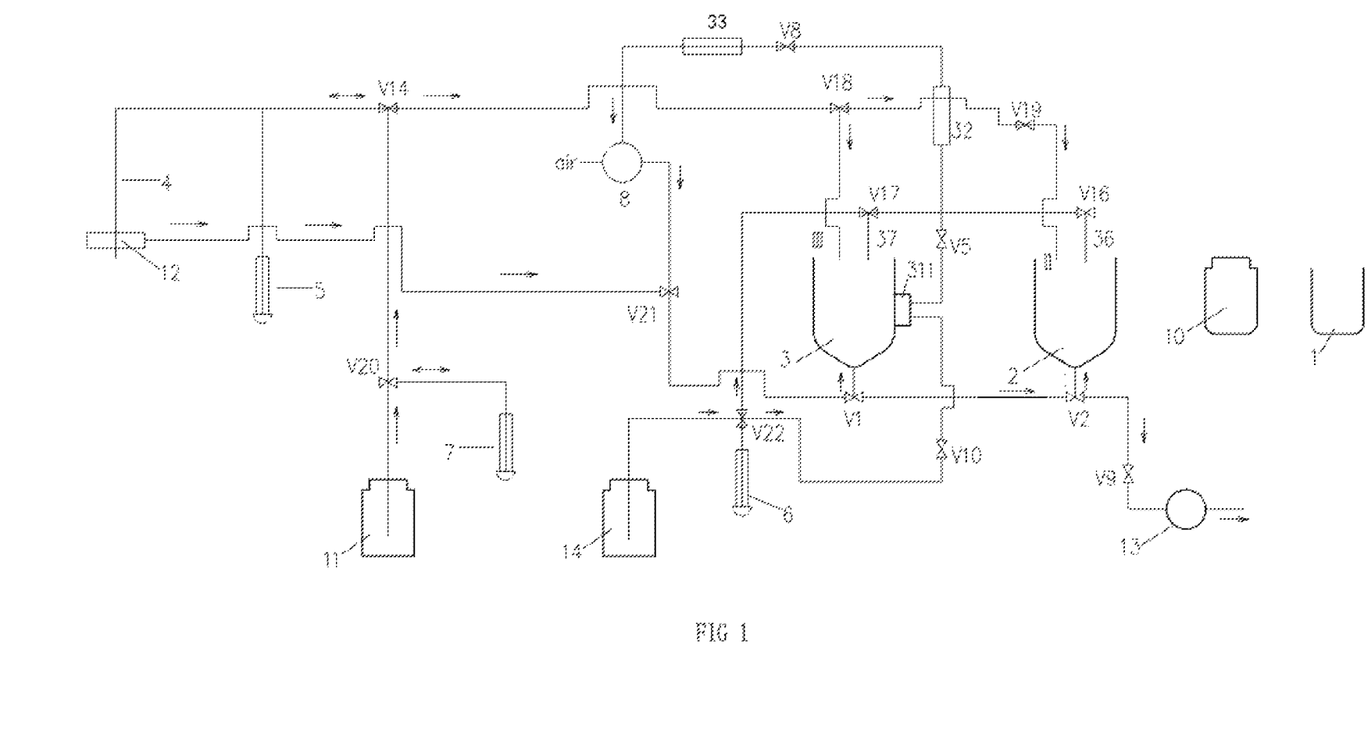
FIG. 1 is a schematic diagram of the instrument structure described in the present invention.
Figure 2A:
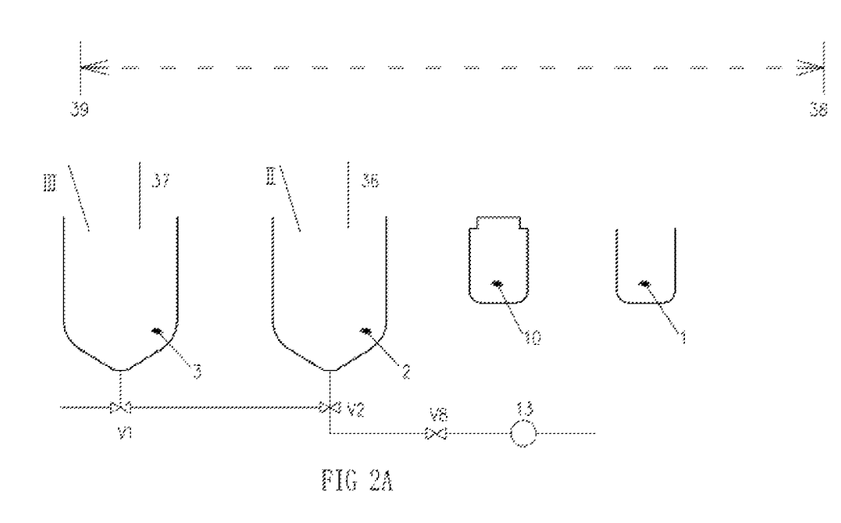
FIG. 2A is a brief drawing of the position relations of the vessels, reagents and the track of the sample needle.
Figure 2B:
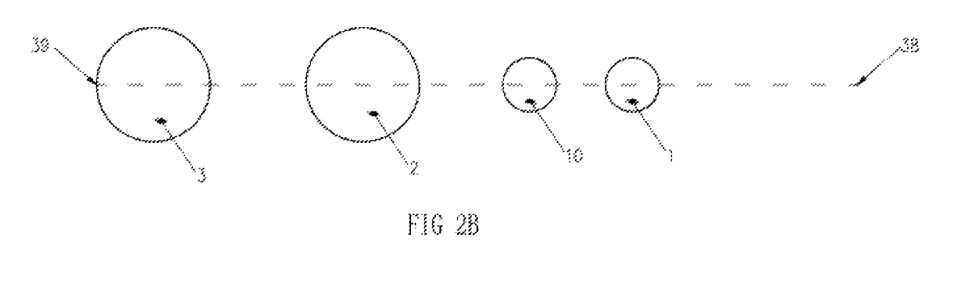
FIG. 2B is the vertical view of FIG. 2A.
Figure 3A:
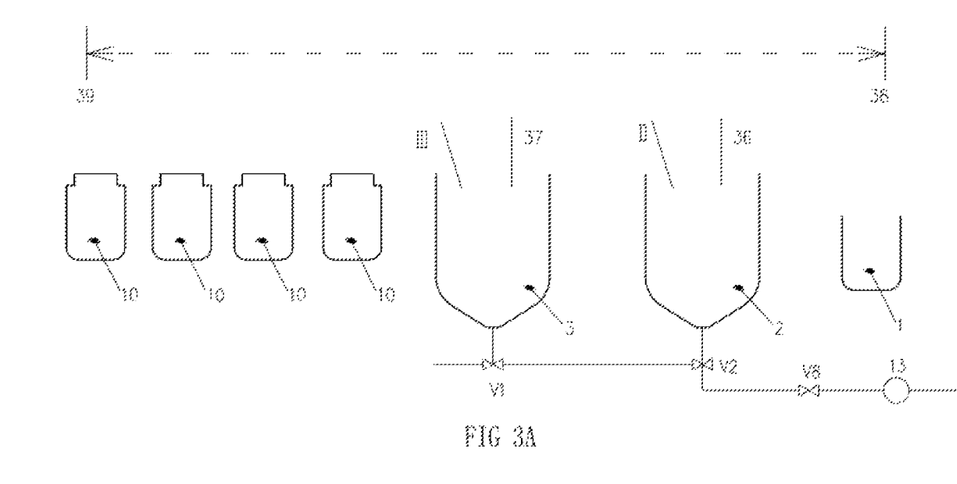
FIG. 3A a brief drawing of the position relations of the vessels, reagents and the track of the sample needle, which is different from FIG. 2.
Figure 3B:
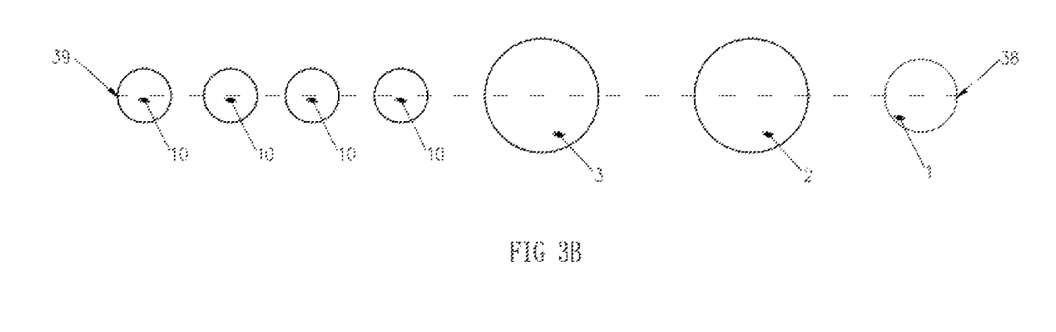
FIG. 3B is the vertical view of FIG. 3A.
Figure 4:
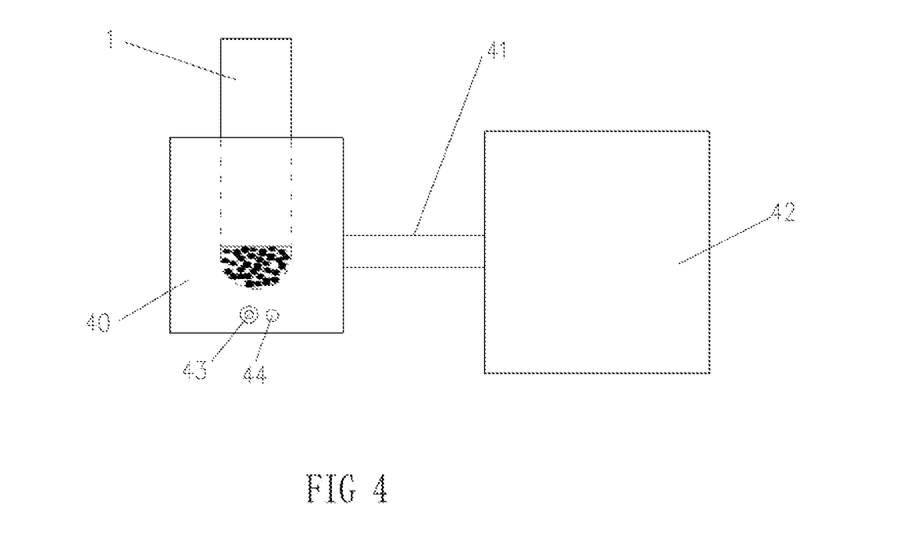
FIG. 4 a brief drawing of the sample holder/sampling vessel.

As shown in FIG. 1, the present invention disclose an automated platelet function analyzer comprising a sampling vessel 1, a preparation vessel 2, an analysis vessel 3, a sampling needle 4, a blood sample syringe 5, a detergent syringe 6, an analysis solution syringe 7 and blood mixing devices 8. The sampling vessel is used to store blood samples and the aggregation. The preparation vessel is used for first dilution of the blood samples. The analysis vessel is used for the second dilution and the platelet number detection. The blood mixing device 8 is an air pump and is used to mix the blood samples in the preparation vessel and the analysis vessel, and it is also used to make a vacuum at 33. The sample syringe connected to the sample needle is used to take sample from sampling vessel to preparation vessel and to analysis vessel, and it also used to take platelet agonist into the sampling vessel. The analysis solution syringe connected to the analysis solution container 11 is used to inject analysis solution to the preparation vessel or analysis vessel. The sampling needle, the blood sample syringe, the platelet agonist syringe, and the analysis solution syringe are driven by motors. The sampling needle is connected to the blood sample syringe and the analysis solution syringe through pipes and valves. After the sampling needle is connected with blood samples syringe, the sampling needle dispenses blood samples to the sampling vessel, absorbs the blood samples from the sampling vessel and transfers the blood samples to the preparation vessel. Absorbing the diluted blood samples from preparation vessel and transferring the diluted blood samples to the analysis vessel are carried out in sequence. After the analysis solution syringe is connected to the sampling needle, the sampling needle will be cleaned.

The mixing device is air pump, which is separately connected to the preparation vessel and the analysis vessel through pipes and valves.

The internal diameter of the pipe, which connected to the preparation vessel and the analysis vessel, is 0.2 mm-2 mm, and the inlet air flow rate is 1-2000 ml/min.

The present invention includes a cleaner 12, which is used to clean the sampling needle outer surface.

The present invention includes a waste liquid pump 13, which is connected to the preparation vessel, the analysis vessel and the cleaner.

The present invention also discloses a platelet analysis method which includes the following steps:
Step 1: connecting the sampling needle with blood sample syringe, absorbing the blood sample, transferring it to the sampling vessel and mixing it;
Step 2: by using the blood sample syringe and the sampling needle quantitatively absorbing the blood sample from the sampling vessel, transferring it to the preparation vessel;
Step 3: analysis syringe dispenses analysis solution into preparation vessel to make the first dilution and mixture of the blood sample;
Step 4: connecting the sampling needle to the blood sample syringe, quantitatively absorbing the blood sample from the preparation vessel and transferring it to the analysis vessel;
Step 5: quantitatively making a second dilution by transferring the analysis solution to the analysis vessel through analysis solution syringe and mixing the blood sample;
Step 6: counting the original platelet numbers of the blood sample in the analysis vessel;
Step 7: dispensing platelet agonist into the sampling vessel by the platelet agonist syringe and mixing the blood sample;
Step 8: repeating step 2 to step 5 with a certain interval and counting the platelet numbers in the blood sample at each time point after adding platelet agonist;
Step 9: comparing the numbers of platelet after dispensing platelet agonist at each time point with that of original platelet to achieve the platelet aggregation rate.

Preferably the present invention adopts the blowing-air method to mixed blood sample.

Example 1

As shown specifically in FIG. 1, the automated platelet function analyzer described in this example includes a sampling vessel 1 and a platelet agonist storage container 10.

A preparation vessel 2 is connected to analysis solution storage container 11 through analysis solution pipeline II, valve V19, valve V18, valve V14 and valve V20. The preparation vessel 2 is connected to a detergent storage container 14 through detergent pipeline 36, valve V16, valve V17 and valve V22. The bottom of the preparation vessel 2 is connected to the air pump 8 through valve V2, valve V1 and valve V21 and to the waste liquid pump 13 through valve V2 and valve V9 respectively.

An analysis vessel 3 is a combination of a set of equipment, which is applied in Sysmex hematology analyzer "KX-21". Certainly you also can use specific structure in the following description. Both of them are based on the same principle. In terms of this embodiment, the analysis vessel 3 mainly includes vessel body, analysis hole 311, quantitative device 32 and vacuum vessel 33. The analysis vessel 3 is connected to analysis solution storage container 11 through analysis solution pipeline III, valve V18, valve V14 and valve V20. The analysis vessel 3 is connected to detergent storage container 14 through detergent pipeline 37, valve V17 and valve V22. The bottom of the analysis vessel 2 is connected to the air pump 8 through valve V1 and valve V21 and to the waste liquid pump 13 through valve V1, valve V2 and valve V9 respectively.

At the bottom of sidewall of the analysis vessel body is an analysis hole 311. The analysis hole 311 is connected to a quantitative device 32 through valve V5 and to the cleaning solution storage container 14 through valve V10. The quantitative device 32 is connected to the air pump 8 and the vacuum vessel 33 through valve V8. Detergent in the detergent storage container 14 is used to clean quantitative device 32 and vacuum vessel 33.

The sampling needle 4 is connected to the analysis solution storage container 11 through valve V14 and valve V20. A cleaner 12 used for sampling needle cleaning is connected to the waste liquid pump 13 through valve V21, valve V1, valve V2 and valve V9.

The blood sample syringe 5 used for absorbing and injecting sample/platelet agonist is connected to the sampling needle and valve V14 respectively. The analysis solution syringe 7 used for absorbing and injecting analysis solution is connected to valve V20. The detergent syringe 6 used for absorbing and injecting detergent is connected to valve V22.

In this embodiment without special description components are connected directly by pipelines.

Figure 5:
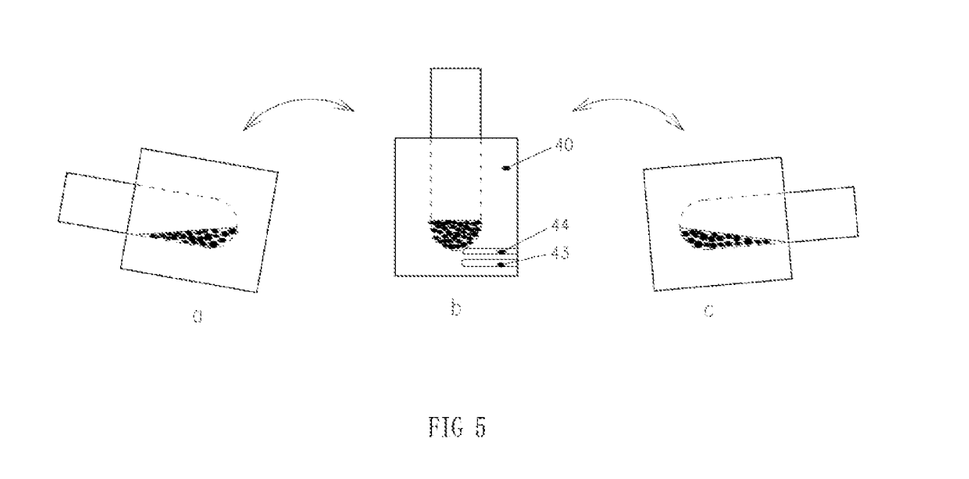
FIG. 5 a brief drawing to show how the sample holder/sampling vessel work.

The process for the usage of this example:
Step 1: A 200-500 uL whole blood sample from vacuum tube with sodium citrate (not shown in the figure) is transferred to sampling vessel 1. Then the sampling vessel 1 is placed on the position of sample holder 40, and the sample holder 40 starts to vacillate left and right and each side is within the angle 90° (shown in FIG. 5), which can make the blood in the sampling vessel 1 well mixed.
Step 2: The sampling needle 4 moves into the sampling vessel 1 by a controlling motor (not shown in the figure). A 10-30 uL well mixed blood sample is absorbed from the sampling vessel 1 by the blood sample syringe 5 and then was injected to the preparation vessel 2 by controlling the valve V14.
Step 3: The analysis solution syringe 7 absorbs analysis solution from analysis solution storage container 11 when they are connected which is controlled by valve V20. Then by controlling the valve V20, valve V14, valve V18 and valve V19, the analysis solution syringe 7 and the analysis solution pipe II are connected. 1-5 ml analysis solution in the analysis solution storage container 7 is transferred to the preparation vessel 2 for the first dilution. The air pump 8 injects air to the bottom of preparation vessel 2 to mix the first dilution sample by controlling valve V21, valve V1 and valve V2. During this time the cleaner 12 on the outer surface of the sampling needle 4 washes the outer surface of the sampling needle with analysis solution to remove residual blood by controlling valve V14, valve V21, valve V1, valve V2 and valve V9. The cleaner 12 washes the inner surface of the sampling needle 4 with analysis solution by the controlling sampling syringe 5 or analysis solution syringe 7.

Step 4: The sampling needle 4 works with the blood sample syringe 5 together. The sampling needle 4 is moved into the preparation vessel, 10-30 uL of the first dilution blood sample is absorbed from the preparation vessel 2 and transferred to the analysis vessel 3 by sampling syringe 5.

Step 5: The analysis solution syringe 7 absorbs analysis solution from analysis solution storage container 11 when they are connected which is controlled by valve V20. Then by controlling the valve V20, valve V14 and valve V18, the analysis solution syringe 7 and the analysis solution pipe III are connected. 1-5 ml analysis solution in analysis solution storage container 7 is transferred to the analysis vessel 3 for the second dilution. Air pump 8 injects air to the bottom of analysis vessel 3 to mix the second dilution sample by controlling valve V21 and valve V1. The air pump 8 vacuums the vacuum vessel 33 to form a negative pressure by valve V8 and vacuum vessel absorbs the blood sample of the secondary dilution in the analysis vessel 3 from the analysis hole 311 by the valve V3 and the valve V8. The quantitative device 32 ensures that the same amount of liquid is absorbed out each time.

Step 6: The original platelet count of the blood sample in the analysis vessel is determined. When test is finished, the detergent syringe 6 adds 4 ml detergent in the detergent storage container 14 into the preparation vessel 2 and the analysis vessel 3 respectively by controlling valve V22, valve V17, and valve V16. Then the detergent is discharged by controlling valve V1, valve V2, valve V9 and waste liquid pump 13. After that, the analysis solution syringe 7 adds 4 ml analysis solution in the analysis solution storage container 11 into the preparation vessel 2 and the analysis vessel 3 respectively by controlling valve V20, valve V14, valve V18, and valve V19. Then the analysis solution is discharged by controlling valve V1, valve V2, valve V9 and waste liquid pump 13.

Step 7: The sampling needle 4 moves into the platelet agonist storage container 10 by the controlling motor (not shown in the figure). 10-50 uL platelet agonist is absorbed from platelet agonist storage container 10 and injected into sampling vessel 1 by the blood sample syringe 5. The sampling vessel 1 placed on the position of sample holder 40 keep swinging from side to side.

Step 8: Step 2-5 are repeated several times every 60 s. The blood sample mixed with platelet agonist is drawn into the preparation vessel 2 and analysis vessel 3 in sequence, which is the same procedure described in step 6. The platelet count is determined in analysis vessel 3 at each time point.

Step 9: The platelet count of the blood sample at each time point after the blood mixed with platelet agonist are compared with the initial platelet count to calculate platelet aggregation rate.

In this embodiment analysis solution should been maintained at a constant temperature (a certain temperature between 18-39° C. Temperature changes of reagent should not be larger than ±1.5° C. A constant temperature can be achieved by previously heating reagent bottles, providing pipes at the early position of preparation vessel and analysis vessel with heating device, or combined previously heated reagent bottles and heated pipes and coupled constant temperature facilities with sampling needle, sampling vessel, preparation vessel and analysis vessel to make sure the temperature is not lower than 18° C. during the analysis. Temperature changes of various aspects should not be larger than ±1.5° C. Means to achieve the goal can be by adding constant temperature facilities of all related components or designing constant temperature equipment inside the instrument Example 2

The repeatability of platelet aggregation rate measured by an automated platelet function analyzer and the comparison of platelet aggregation rate with turbidimetric method.

Comparison between the repeatability of results from an automated analyzer according to the present invention and that from a kind of instrument based on the principle of turbidimetric method (The turbidimetric method refers to: Born GVR. Aggregation of blood platelets by adenosine diphosphate and its reversal. Nature (Lond.). 1962; 194: 927)

Using one whole blood sample with citrate sodium as anticoagulant, the platelet aggregation rates from 0 to 5 min are determined respectively by the analyzer according to the present invention and turbidimetric method instrument. The repeated 10 results showed in the table below.

The instrument mentioned in this embodiment is the same as that mentioned in example 1. Operation steps is also the same as that mentioned in embodiment 1. Analysis solution is physiological saline. Platelet agonist is diphosphate adenosine aqueous solution. The first dilution ratio is 240 times, and the second dilution ratio is 240 times.

TABLE 1

The platelet aggregation rate from 1 to 5 minutes determined from the instrument according to the present invention (instrument model: PL-11)

| items | Original platelet count ($\times 10^9$/L) | The platelet aggregation rate (%) | | | | |
|---|---|---|---|---|---|---|
| | | 1 min | 2 mins | 3 mins | 4 mins | 5 mins |
| test1 | 145 | 35.0 | 43.0 | 54.6 | 62.3 | 61.4 |
| Test2 | 142 | 34.6 | 40.6 | 52.8 | 65.8 | 67.3 |
| Test3 | 140 | 36.3 | 45.5 | 56.2 | 60.1 | 65.5 |
| Test4 | 146 | 33.6 | 41.9 | 55.4 | 64.5 | 63.8 |
| Test5 | 142 | 38.9 | 47.0 | 57.6 | 65.4 | 64.7 |
| Test6 | 148 | 37.1 | 42.5 | 55.9 | 60.1 | 62.3 |
| Test7 | 141 | 34.3 | 44.6 | 55.4 | 62.5 | 60.8 |
| Test8 | 150 | 35.6 | 41.0 | 53.2 | 64.0 | 62.4 |
| Test9 | 144 | 33.2 | 46.2 | 57.6 | 59.9 | 63.9 |
| Test10 | 151 | 34.8 | 44.1 | 55.1 | 62.4 | 64.8 |
| CV | — | 4.8% | 4.7% | 2.9% | 3.5% | 3.1% |

According to the 10 testing results the SD and average value at each minutes is worked out, then the Coefficient of Variation (CV)

CV=SD/average value×100%

In 1-5 min, all the repeatability of the 10 testing result of the platelet aggregation rate (Represented in CV) is not more than 5%, suggesting that the instrument possesses a reliable reproducibility in the use for determining platelet aggregation rate,

TABLE 2

The results of platelet aggregation rate (A platelet aggregation analyzer based on turbidimetric method)

| items | The platelet aggregation rate (%) | | | | |
|---|---|---|---|---|---|
| | 1 min | 2 mins | 3 mins | 4 mins | 5 mins |
| test1 | 24.5 | 29.0 | 36.6 | 50.3 | 50.4 |
| Test2 | 20.6 | 35.6 | 44.8 | 43.8 | 57.3 |

TABLE 2-continued

The results of platelet aggregation rate (A platelet aggregation analyzer based on turbidimetric method)

| items | The platelet aggregation rate (%) | | | | |
|---|---|---|---|---|---|
| | 1 min | 2 mins | 3 mins | 4 mins | 5 mins |
| Test3 | 20.3 | 40.5 | 38.2 | 48.1 | 49.5 |
| Test4 | 18.9 | 26.9 | 37.4 | 55.5 | 53.8 |
| Test5 | 26.5 | 32.0 | 49.6 | 46.8 | 46.7 |
| Test6 | 20.6 | 30.4 | 42.6 | 50.5 | 50.5 |
| Test7 | 27.1 | 35.1 | 34.3 | 45.6 | 55.9 |
| Test8 | 23.5 | 28.2 | 32.8 | 43.3 | 54.3 |
| Test9 | 22.6 | 27.8 | 37.8 | 36.9 | 57.1 |
| Test10 | 19.2 | 34.6 | 37.6 | 47.6 | 59.5 |
| CV | 13.1% | 13.6% | 12.9% | 10.7% | 7.6% |

The repeatability of the 10 test result of platelet aggregation rate in 1-5 min (represented in CV) is more than 10%, suggesting that instrument base on the turbidimetric method possesses a lower reproducibility than the instrument according to the present invention.

2) Correlation of results from the automated analyzer according to the present invention and turbidimetric method instrument 40 samples are determined by the automated analyzer according to the present invention and traditional turbidimetric instrument simultaneously. Maximum of platelet aggregation rate from the 40 samples is as follows:

TABLE 3

Comparison of the maximum platelet aggregation rate from automated analyzer according the present invention and turbidimetric instrument

| sample | Maximum platelet aggregation rate (%) | |
|---|---|---|
| | automated analyzer according the present invention | a traditional turbidimetric instrument |
| 1 | 75.5 | 61.7 |
| 2 | 56.1 | 50.2 |
| 3 | 54.3 | 48.1 |
| 4 | 66.8 | 59.3 |
| 5 | 45.2 | 36.5 |
| 6 | 69.1 | 61.5 |
| 7 | 77.2 | 63.7 |
| 8 | 48.1 | 40.8 |
| 9 | 28.5 | 23.1 |
| 10 | 78.7 | 62.9 |
| 11 | 65.2 | 58.2 |
| 12 | 51.2 | 40.8 |
| 13 | 49.4 | 34.8 |
| 14 | 62.3 | 49.2 |
| 15 | 51.5 | 44.3 |
| 16 | 65.6 | 53.9 |
| 17 | 54.2 | 43.9 |
| 18 | 46.8 | 42.6 |
| 19 | 78.4 | 62.2 |
| 20 | 68.9 | 54.6 |
| 21 | 43.6 | 33.5 |
| 22 | 65.9 | 59.1 |
| 23 | 69.6 | 55.8 |
| 24 | 39.2 | 30.3 |
| 25 | 45.8 | 40.4 |
| 26 | 57.6 | 45.9 |
| 27 | 49.2 | 39.1 |
| 28 | 46.5 | 39.1 |
| 29 | 54.8 | 49.2 |
| 30 | 34.6 | 25.9 |
| 31 | 63.8 | 57.8 |
| 32 | 68.6 | 59.1 |
| 33 | 54.2 | 47.5 |
| 34 | 53.0 | 39.8 |

TABLE 3-continued

Comparison of the maximum platelet aggregation rate from automated analyzer according the present invention and turbidimetric instrument

| sample | Maximum platelet aggregation rate (%) | |
|---|---|---|
| | automated analyzer according the present invention | a traditional turbidimetric instrument |
| 35 | 62.8 | 44.6 |
| 36 | 51.2 | 37.8 |
| 37 | 65.9 | 48.9 |
| 38 | 59.3 | 53.7 |
| 39 | 58.2 | 52.8 |
| 40 | 46.8 | 42.6 |
| Average platelet aggregation rate | 57.1 ± 11.9 | 47.4 ± 10.5 |

Figure 6:
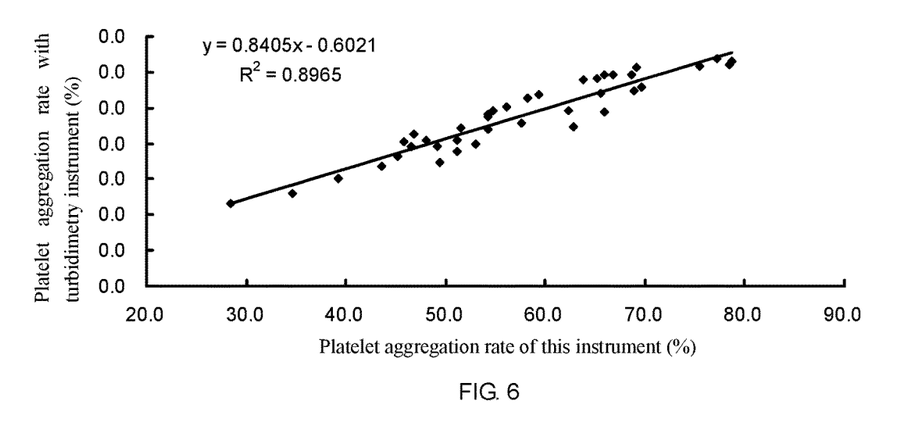
FIG. 6 is a correlation analysis of maximum platelet aggregation rate of the instrument described in the present invention and turbidimetry instrument.

The scatter chart was drawn with determination results of the automated analyzer as x-axis, and determination results of turbidimetric method instrument as y-axis. Meanwhile through linear regression analysis FIG. 6 is drawn. According to the results of FIG. 6, determination results from the two methods have a good correlation. Correlation coefficient is $R^2=0.8965$, $R=0.9468$. But the determination results of the automated analyzer according to the present invention are higher than that of turbidimetric instrument. There is significant differences between them ($P<0.05$).

The automated platelet function analyzer according to the present invention can determine multiple parameters such as the numbers of platelet, mean platelet volume, platelet volume distribution, platelet aggregation rate (including platelet aggregation rate in different time, the maximum aggregation rate and the maximum aggregation time) and so on automatically and simultaneously. The test items are more efficient and more comprehensive. The automated analyzer can add platelet agonist automatically. Therefore, the instrument has the ability to obtain the platelet aggregation results at each time point by the direct detection of platelet changes before and after adding platelet agonist.

The present invention provides an idea for designing an automated platelet function analyzer and its analytical methods.

While preferred embodiments of the invention have been shown and described, there are many ways to realize this technical program. It will be obvious to those skilled in the art that changes and modifications may be made without departing from the invention in its broader aspects, and therefore, the aim in the appended claims is to cover all such changes and modifications as fall within the true spirit and scope of the invention. Other parts not expressed in the embodiments can be achieved with existing technology.

The invention claimed is:

1. An automated platelet function analyzer comprising:
a sampling vessel, a preparation vessel, an analysis vessel, a sampling needle, a blood sample syringe, a detergent syringe, an analysis solution syringe, a blood mixing device and a sample holder configured to vacillate left and right within a 90° angle;
the sampling vessel is configured to store blood samples and agonist for platelet aggregating;
the preparation vessel is configured for a first blood sample dilution;
the analysis vessel is configured for a second blood sample dilution and platelet number measure;
the blood mixing device, which is an air pump connected to a bottom of the preparation vessel and to a bottom of the analysis vessel through pipes and valves, is configured for mixing blood samples in the preparation vessel and the analysis vessel;

the blood sample syringe is connected with the sampling needle, the sampling needle being movable to the sampling vessel, an agonist storage container, the preparation vessel and the analysis vessel, wherein the sampling needle is configured to take a sample from the sampling vessel to the preparation vessel and the analysis vessel, and also the sampling needle is configured to take and dispense platelet agonist into the sampling vessel;

the analysis solution syringe is connected with an analysis solution storage container so as to dispense the analysis solution into the preparation vessel or the analysis vessel;

the sampling needle, the sample syringe, the detergent syringe and the analysis solution syringe are driven by separate motors;

the sampling needle is connected to the blood sample syringe and the analysis solution syringe through pipes and valves respectively;

the detergent syringe is connected to a detergent storage container through a detergent pipeline and valves, respectively, the analysis vessel and the preparation vessel are connected to the detergent storage container through another detergent pipeline and valves, respectively; and with the blood sample syringe connected to the sampling needle, the blood sample syringe and the sampling needle are configured to operate in sequence transferring the blood samples to the sampling vessel, absorbing a partial blood sample from the sampling vessel and transferring the partial blood sample to the preparation vessel, absorbing the diluted blood sample from the preparation vessel and transferring the diluted blood sample to the analysis vessel.

2. The automated platelet function analyzer according to claim 1, wherein the pipe, which is connected to the preparation vessel and the analysis vessel, has an internal diameter of 0.2 mm to 2 mm, and an inlet air flow rate is 1-1000 ml/min.

3. The automated platelet function analyzer according to claim 1, wherein the air pump is a rotary pump or a syringe.

4. The automated platelet function analyzer according to claim 1, further comprising a cleaner configured to clean the outer surface of the sampling needle.

5. The automated platelet function analyzer according to claim 4, further comprising a waste liquid pump connected to the preparation vessel, the analysis vessel and the cleaner.

6. The automated platelet function analyzer according to claim 1, further comprising fewer than five agonist storage containers.

7. The automated platelet function analyzer according to claim 1, wherein the sampling vessel is placed in the sample holder, and the sample holder is equipped with a heater and a temperature control.

8. The automated platelet function analyzer according to claim 1, wherein the sampling vessel is a single used cuvette and is kept open during the testing process.

9. The automated platelet function analyzer according to claim 1, wherein the air pump is connected to a vacuum vessel configured to form a negative pressure such that the vacuum vessel is configured to absorb a blood sample of a secondary dilution in the analysis vessel from an analysis hole in the analysis vessel.

* * * * *